United States Patent [19]

Ofuchi et al.

[11] Patent Number: 5,214,052

[45] Date of Patent: May 25, 1993

[54] METHOD FOR DISSOLVING ARGININEAMIDES AND PHARMACEUTICAL COMPOSITIONS CONTAINING THEM

[75] Inventors: Kunihiko Ofuchi; Tatsuo Nomura, both of Hasaki, Japan

[73] Assignee: Mitsubishi Kasei Corporation, Tokyo, Japan

[21] Appl. No.: 851,248

[22] Filed: Mar. 13, 1992

Related U.S. Application Data

[63] Continuation of Ser. No. 577,042, Aug. 30, 1990, abandoned, which is a continuation of Ser. No. 223,152, Jul. 22, 1988, abandoned.

[30] Foreign Application Priority Data

Jul. 28, 1987 [JP] Japan .................... 62-188484

[51] Int. Cl.$^5$ .................... A61K 9/08; A61K 31/445; A61K 47/00
[52] U.S. Cl. .................... 514/315; 514/23; 514/53
[58] Field of Search ...................... 514/315

[56] References Cited

U.S. PATENT DOCUMENTS

| | | | |
|---|---|---|---|
| 2,854,380 | 9/1958 | Jensen et al. | 167/67 |
| 4,066,773 | 1/1977 | Okamoto et al. | 424/267 |
| 4,101,653 | 7/1978 | Okamoto et al. | 424/177 |
| 4,117,127 | 9/1978 | Okamoto et al. | 424/247 |
| 4,131,673 | 12/1978 | Okamoto et al. | 424/247 |
| 4,201,863 | 5/1980 | Okamoto et al. | 546/166 |
| 4,258,192 | 3/1981 | Okamoto et al. | 546/166 |
| 4,870,175 | 9/1989 | Suzuki et al. | 544/354 |
| 5,013,723 | 5/1991 | Sisto et al. | 514/19 |

OTHER PUBLICATIONS

Remington's Pharmaceutical Sciences, 15th Ed. (1975) Mack Pub. Co., Easton, Pa. pp. 240-244.
Blodinger—Formulation of Veterinary Dosage Forms, Marcel Dekker, Inc., N.Y. & Basel, pp. 152-155.
Gstirner F.: "Einfuhrung in die Verfahrenstechnik der Arzneiformung" 1973 pp. 271-272.

*Primary Examiner*—Shep K. Rose
*Attorney, Agent, or Firm*—Oblon, Spivak, McClelland, Maier & Neustadt

[57] ABSTRACT

A method for dissolving an arginineamide of the invention comprising dissolving N$^2$-arylsulfonyl-L-arginineamide having the general formula (I)

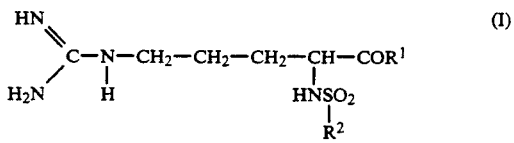

wherein R$^1$ represents a (2R, 4R)-4-alkyl-2-carboxypiperizino group and R$^2$ represents a phenyl group or a condensed polycyclic compound residue which may be substituted with one or more substituents selected from lower alkyl groups, lower alkoxy groups and lower alkyl-substituted amino groups, said condensed polycyclic compound residue including a benzene ring which binds to sulfur atom of the sulfonyl group in the general formula (I) and is condensed with one or more other rings which may be heterocyclic and having 7 to 14 carbon atoms as the ring-constituent atoms; and/or its salt in a solvent of alcohol and water is disclosed herein.

And, the pharmaceutical composition comprising N$^2$-arylsulfonyl-L-arginineamide having the general formula (I), an alcohol and water is disclosed herein.

4 Claims, 3 Drawing Sheets

METHOD FOR DISSOLVING ARGININEAMIDES AND PHARMACEUTICAL COMPOSITIONS CONTAINING THEM

This application is a continuation of application Ser. No. 07/577,042, filed on Aug. 30, 1990, now abandoned, which is a continuation of abandoned application Ser. No. 07/223,152 filed Jul. 22, 1988.

FIELD OF THE INVENTION

The invention relates to a method for dissolving arginineamides and pharmaceutical compositions containing them.

BACKGROUND OF THE INVENTION

Arginineamides are known to have anti-thrombotic activities and are expected to be used as anti-thrombotic agents (please refer to Japanese Patent No. 1382377). However, it is very difficult to obtain a solution containing any of arginineamides at high concentration due to poor solubility in water and therefore any of these compounds is not suitable for applying as the injection containing it at high concentration.

An object of the invention is to provide a method for improving the solubilities of arginineamides so as to apply as the injections containing them at high concentration.

SUMMARY OF THE INVENTION

The invention provides a method for dissolving arginineamide comprising dissolving $N^2$-arylsulfonyl-L-arginineamide having the general formula (I)

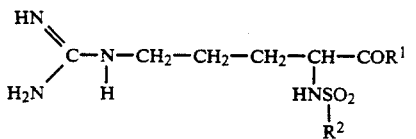

wherein $R^1$ represents a (2R, 4R)-4-alkyl-2-carboxypiperidino group and $R^2$ represents a phenyl group or a condensed polycyclic compound residue which may be substituted with one or more substituents selected from lower alkyl groups, lower alkoxy groups and lower alkyl-substituted amino groups, said condensed polycyclic compound residue including a benzene ring which binds to sulfur atom of the sulfonyl group in the general formula (I) and is condensed with one or more other rings which may be heterocyclic and having 7 to 14 carbon atoms as the ring-constituent atoms;

and/or its salt in a solvent of alcohol and water. Further, the invention provides pharmaceutical compositions containing arginineamides.

BRIEF DESCRIPTION OF THE DRAWINGS

A more complete understanding of the invention and many of the attendant advantages thereof will be readily obtained as the same becomes better understood by reference to the following detailed description when considered in connection with the accompanying drawings, wherein.

Figure 1:
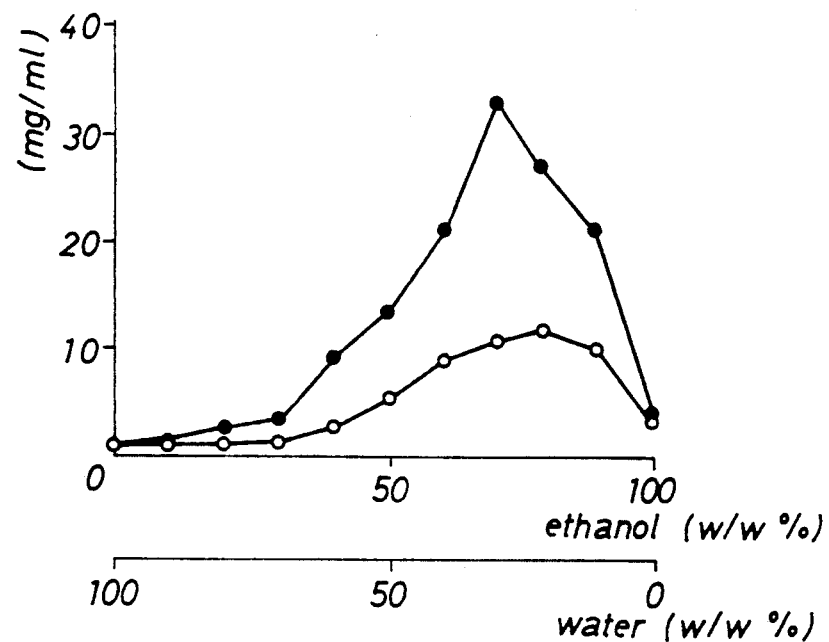
FIG. 1 is a graph showing the solubility of argipidine in solvent (mg/ml) over a range of ethanol-water solvent mixture.

DETAILED DESCRIPTION OF THE INVENTION $R^1$ in the general formula (I) represents a (2R, 4R)-4-alkyl-2-carboxypiperidino group. The alkyl herein is a lower alkyl having 1 to 5 carbon atoms such as methyl, ethyl, propyl, isopropyl and butyl. Preferably, $R^1$ represents a (2R, 4R)-4-methyl-2-carboxypiperidino group.

$R^2$ in the general formula (I) represents a phenyl group or a condensed polycyclic compound residue. The condensed polycyclic compound residue defines herein that it includes a benzene ring which binds to sulfur atom of the sulfonyl group in the general formula (I) and is condensed with one or more other rings which may be heterocyclic and it has 7 to 14 carbon atoms as the ring-constituent atoms. The benzene ring included in the condensed polycyclic compound residue binds to sulfur atom of the sulfonyl group in the general formula (I), provided that the position on the benzene ring binding to the sulfur atom is not particularly limited. A heteroatom or heteroatoms constituting the heterocyclic ring may be oxygen, nitrogen or sulfur atom.

Preferable condensed polycyclic compound residue is a dicyclic compound residue including benzene ring condensed with one other ring, preferably one five- or six-membered ring which may be heterocyclic or a tricyclic compound residue including benzene ring condensed with two other rings, preferably two five or six-membered rings which may be heterocyclic. The examples of such condensed polycyclic compound residues include anthryl, phenanthryl, benzofuranyl, dibenzothienyl, phenoxthinyl, quinolyl, carbazolyl, acridinyl, phenazinyl, phenothiazinyl, phenoxazinyl, benzimidazolyl, fluorenyl, 2,3-dihydrobenzofuranyl, thioxathenyl, naphthyl, tetrahydronaphthyl, isoquinolyl, tetrahydroquinolyl and tetrahydroisoquinolyl.

If desired, $R^2$ can be substituted with one or more substituents selected from lower alkyl groups, lower alkoxy groups and lower alkyl-substituted amino groups. The lower alkyl group is alkyl group having 1 to 5 carbon atoms, such as methyl, ethyl, propyl, isopropyl, butyl, isobutyl and tert-butyl. The lower alkoxy group is alkoxy group having 1 to 5 carbon atoms, such as methoxy, ethoxy, propoxy, isopropoxy and butoxy. And, the lower alkyl-substituted amino group is the amino group substituted with the above-mentioned lower alkyl group, such as alkylamino and dialkylamino.

Preferably, $R^2$ represents 3-methyl-1,2,3,4-tetrahydro-8-quinolyl group.

As the arginineamides used in the invention, the following compounds are exemplified.

(2R, 4R)-1- [$N^2$-(3-isopropoxybenzenesulfonyl)-L-arginyl]-4-methyl-2-piperidinecarboxylic acid;

(2R, 4R)-1- [$N^2$-(3,5-dimethyl-4-propoxybenzenesulfonyl)-L-arginyl]-4-methyl-2-piperidinecarboxylic acid;

(2R, 4R)-1- [$N^2$-(5,6,7,8-tetrahydro-2-naphthalenesulfon)-yl)-L-arginyl]-4-methyl-2-piperidinecarboxylic acid;

(2R, 4R)-1-[$N^2$-(5-dimethylamino-1-naphthalenesulfonyl)-L-arginyl]-4-methyl-2-piperidinecarboxylic acid;

(2R, 4R)-1-[N²-(3-methyl-1,2,3,4-tetrahydro-8-quinoline-sulfonyl)-L-arginyl]-4-methyl-2-piperidinecarboxylic acid;

(2R, 4R)-1-[N²-(2-dibenzothiophenesulfonyl)-L-arginyl]-4-methyl-2-piperidinecarboxylic acid;

(2R, 4R)-1-[N²-(2,4-dimethoxy-3-butoxybenzenesulfonyl)-L-arginyl]-4-methyl-2-piperidinecarboxylic acid;

(2R, 4R)-1-[N²-(3,5-dimethyl-4-propoxybenzenesulfonyl)-L-arginyl]-4-methyl-2-piperidinecarboxylic acid;

(2R, 4R)-1-[N²-(3-ethyl-1,2,3,4-tetrahydro-8-quinoline-sulfonyl)-L-arginyl] 4-methyl-2-piperidinecarboxylic acid;

(2R, 4R)-1-[N²-(2-carbazolesulfonyl)-L-arginyl]-4-methyl-2-piperidinecarboxylic acid;

(2R, 4R)-1-[N²-(2-fluorenesulfonyl)-L-arginyl]-4-methyl2-piperidinecarboxylic acid;

(2R, 4R)-1-[N²-(2-phenoxthinesulfonyl)-L-arginyl]-4-methyl-2-piperidinecarboxylic acid;

(2R, 4R)-1-[N²-(2-anthracenesulfonyl)-L-arginyl]-4-methyl-2-piperidinecarboxylic acid; and (2R, 4R)-1-[N²-(7-methyl-2 -naphthalenesulfonyl)-L-arginyl]-4- methyl-2-piperidinecarboxylic acid: as well as their 4-ethyl analogues, their 4-propyl analogues, their 4-butyl analogues and their 4-pentyl analogues.

The invention can use the salts of arginineamides having the general formula (I). The salts may be acid addition salts prepared by reacting with any inorganic or organic acids such as hydrochloric acid, hydrobromic acid, hydroiodic acid, sulfuric acid, nitric acid, phosphoric acid, acetic acid, citric acid, maleic acid, succinic acid, lactic acid, tartaric acid, gluconic acid, benzoic acid, methanesulfonic acid, ethanesulfonic acid, benzenesulfonic acid and p-toluenesulfonic acid. Further, the salts may be inorganic or organic salts prepared by reacting organic or inorganic bases such as sodium hydroxide, potassium hydroxide, ammonium hydroxide, triethylamine, procaine, dibenzylamine, N,N'-dibenzylethylenediamine and N-ethylpiperidine.

In the method for dissolving an arginineamide according to the invention, the arginineamide and/or its salt is dissolved in the solvent of alcohol and water. As the alcohols used in the invention, monohydric alcohols such as methanol, ethanol and the like; dihydric alcohols such as ethyleneglycol, propyleneglycol and the like; polyhydric alcohols such as glycerine and the like; and ethers of di- and polyhydric alcohols such as polyethyleneglycol and the like are mentioned. Methanol, ethanol, propyleneglycol and polyethyleneglycol are preferable. Ethanol is particularly preferable. If necessary, a mixture of these alcohols can be used.

Water used in the invention is generally distilled water or purified water, but a physiological saline or Ringer's solution may be used.

The mixed ratio (by weight) of alcohol to water in the above solvent is generally 0.1 to 10, preferably 0.2 to 5 and more preferably 0.3 to 3.

If necessary, any saccharides can be admixed with the solvent of alcohol and water in the invention. As the saccharides used in the invention, monosaccharides, oligosaccharides, polysaccharides and their reduced derivatives (for example sugaralcohol) which are soluble in water are mentioned. Among them, glucose, fructose, maltose, saccharose and D-sorbitol each of which has the high solubility in water are preferable. D-sorbitol is particularly preferable. A mixture of these saccharides may be used.

The mixed ratio (by weight) of saccharide (if present) to water is generally 0.1 to 10, preferably 0.4 to 4 and more preferably 0.5 to 2.

The manner how to dissolve the arginineamide having the general formula (I) in the solvent of alcohol and water and optionally saccharide is not particularly limited. Generally, the saccharide is dissolved in water and then the alcohol is added thereto followed by mixing. Next, the arginineamide is slowly added while stirring until complete dissolution.

The temperature on dissolution is not particularly limited. When the saccharide is dissolved in water, however, it is preferable to war water at 40 to 70° C for accelerating the dissolution rate.

Further, when the volatile alcohol such as ethanol and the like is used, it is necessary to take care for preventing the evaporation of alcohol, for example by cooling the solution to room temperature before the dissolution, or dissolving in a closed container.

The concentration of arginineamide in the solution can be selected within the wide range depending on the intended uses. According to the invention, the solution in which the arginineamide is dissolved at high concentration, for example from several times to several thousands times the solubility of arginineamide in water can be obtained.

The solution containing any of the arginineamide having the general formula (I) in the solvent of alcohol and water and optionally saccharide thus obtained can constitute the pharmaceutical composition of the invention.

The pharmaceutical compositions of the invention are useful for treating thrombosis. Accordingly, the pharmaceutical compositions can be used as the antithrombotic agents.

The pharmaceutical composition of the invention may contain antiseptic, anti-oxidant, soothing agent, pH-controlling agent and the like. And, if necessary any pharmaceutical ingredient(S) other than the arginineamides may be added to form the combined preparation.

The pharmaceutical composition of the invention is injectable as the injection. This injectable composition may contain stabilizer, buffer, preservative and the like which are acceptable for the injection may be added in addition to the above-mentioned ingredients. If desired, the injectable composition according to the invention is prepared to contain the arginineamide at very high concentration, which is used by diluting with water, electrolyte, carbohydrate solution, Ringer's solution or the like on the application such as infusion and dialysis.

Alternatively, the pharmaceutical composition of the invention is topically applicable as the solution for topical application, the ointment or the suppository. When the pharmaceutical composition is used as the solution for topical application, the solution prepared above can be used as it is. And, the ointment or the suppository of the invention may be prepared by dissolving the solution prepared above in the base or the like.

EXAMPLES

The invention will now be further described by the following, non-limiting examples.

Example 1

(2R, 4R)-1-[N² -(3-methyl-1,2,3,4-tetrahydro-8-quinolinesulfonyl)-L-arginyl]-4-methyl-2-piperidinecarboxylic acid ( argipidine ) was dissolved in the solvent of ethanol and water while varying the mixed ratio of ethanol to water at 20° C. ( ) or 5° C. (∘).

The results are shown in FIG. 1. In FIG. 1, the ordinate is the solubility of argipidine in the solvent (mg/ml) and the abscissa is the weight percentages of ethanol and water (w/w %).

As shown in FIG. 1, the solubility of argipidine in the solvent comprising 70 % by weight of ethanol and 30 % by weight of water at 20° C. was 33.23 mg/ml and that at 5° C. was 10.73 mg/ml.

COMPARATIVE EXAMPLE 1

Argipidine was dissolved in the aqueous sorbitol solution while varying the sorbitol concentration at 20° C.

Figure 2:
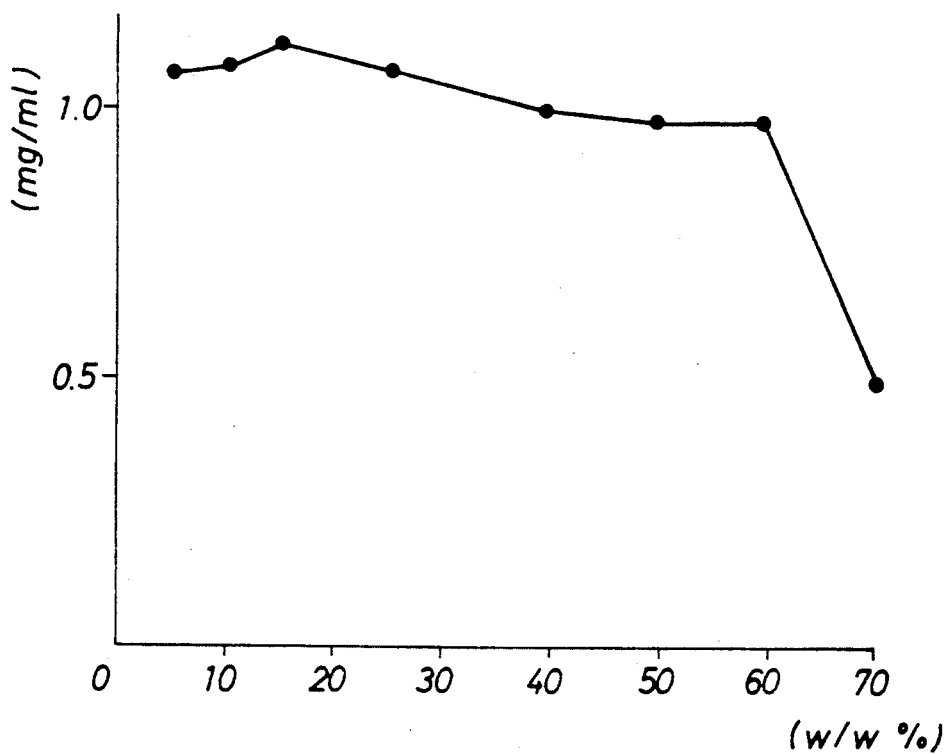
FIG. 2 shows the solubility of argipidine in aqueous sorbitol solution.

The result was shown in FIG. 2. In FIG. 2, the ordinate is the solubility of argipidine in the aqueous sorbitol solution (mg/ml) and the abscissa is the concentration of sorbitol in the aqueous solution (w/w %).

As shown in FIG. 2, the solubility of argipidine in the aqueous sorbitol solution was low and it was the substantially same as the solubility of argipidine in water.

EXAMPLE 2

Argipidine was dissolved in the solvent comprising the aqueous 25 % sorbitol solution (∘), the aqueous 50 % sorbitol solution (□) or the 70 % sorbitol solution (△) and ethanol while varying the mixed ratio of ethanol to the aqueous sorbitol solution at 30° C.

Figure 3:
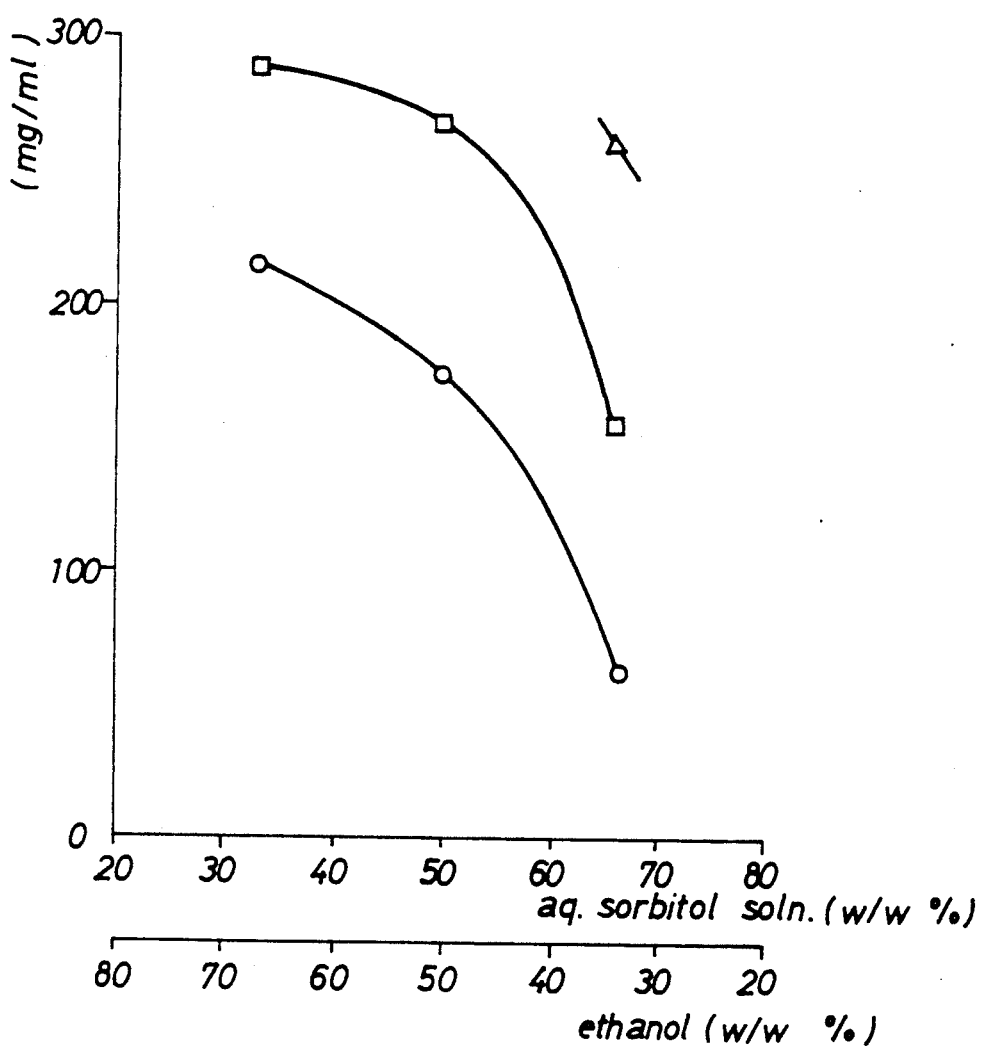
FIG. 3 shows the solubility of argipidine over a range of ethanol-aqueous sorbitol solutions containing different amounts of sorbitol.

The results are shown in FIG. 3. In FIG. 3, the ordinate is the solubility of argipidine in the solvent (mg/ml) and the abscissa is the weight percentages of the aqueous sorbitol solution and ethanol (w/w %).

EXAMPLE 3

Argipidine was dissolved in the solvent comprising the aqueous 33% glucose solution (∘), the aqueous 50% glycerine solution (△), the 50% sorbitol solution ( ) or the aqueous 50% sucrose solution (□) and ethanol while varying the mixed ratio of ethanol to the aqueous solution at 30° C.

Figure 4:
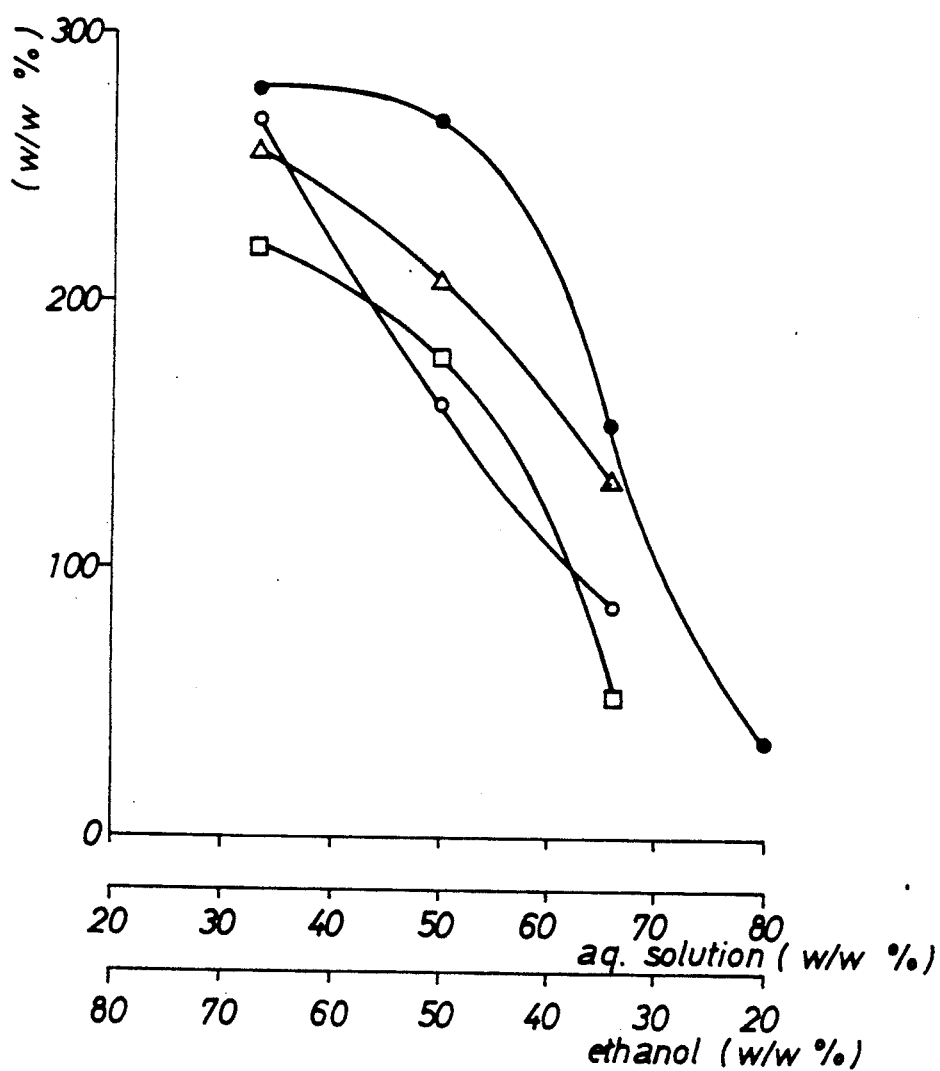
FIG. 4 shows the solubility of argipidine over a range of ethanol-aqueous solutions, wherein the aqueous solutions contain glucose, glycerin, sorbitol or sucrose.

The results are shown in FIG. 4. In FIG. 4, the ordinate is the solubility of argipidine in the solvent (mg/ml) and the abscissa is the weight percentages of the aqueous solution and ethanol (w/w %).

EXAMPLE 4

The distilled water for injection (200 g) was placed in a one-litre beaker, to which D-sorbitol (300 g) was added with stirring and dissolved. At this time, if necessary the solution may be heated. Then, ethanol (400 g) was added and mixed with stirring followed by adding argipidine (100 g) with stirring until complete dissolution.

The thus-obtained solution can be used for dialysis after diluting it with the weak acidic solution containing D-sorbitol.

EXAMPLE 5

The distilled water for injection (200 g) was placed in a one-litre beaker, to which glucose (200 g) was added with stirring and dissolved. Then, ethanol (400 g) was added and mixed with stirring followed by adding argipidine (100 g) with stirring. Further, the distilled water for injection was added till the total volume of the solution became 1 litre.

The thus-obtained solution can be used for drip infusion after diluting it with the aqueous sorbitol solution, the aqueous D-sorbitol solution or Ringer's solution on use.

EXAMPLE 6

The distilled water for injection (200 g) was placed in a one-litre beaker, to which -sorbitol (300 g) was added with stirring and dissolved. At this time, if necessary the solution may be heated. Then, glycerine (200g) and ethanol (200 g) were added and mixed with stirring followed by adding argipidine (100 g) with stirring. Further, the distilled water for injection was added till the total volume of the solution became 1 litre.

The thus-obtained solution can be used for dialyses after diluting the weak acidic solution containing D-sorbitol.

EFFECT OF THE INVENTION

According to the method for dissolving the arginineamide of the invention, the injection containing any of the arginineamides having the general formula (I) and/or their salts, particularly at high concentration can be obtained.

What is claimed is:

1. A method for dissolving an arginineamide, comprising:
dissolving $N^2$-arylsulfonyl-L-argininamide represented by formula (I):

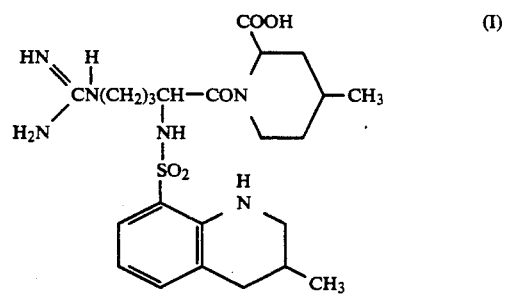

and/or its salt in a solvent containing ethanol, water and a saccharide.

2. The method according to claim 1, wherein the saccharide is at least one member selected from the group consisting of sorbitol, glucose, glycerin and sucrose.

3. A pharmaceutical composition for injection, comprising:
$N^2$-arylsulfonyl-L-argininamide represented by formula (I):

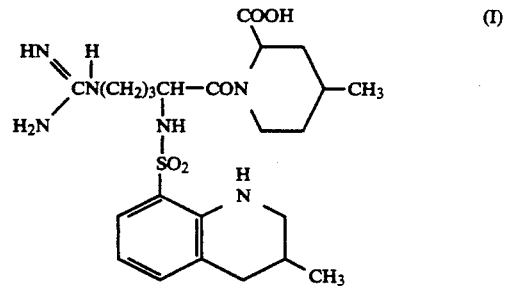

and/or its salt together with ethanol, water and a saccharide.

4. The composition according to claim 3, wherein the saccharide is at least one member selected from the group consisting of sorbitol, glucose, glycerin and sucrose.

* * * * *

UNITED STATES PATENT AND TRADEMARK OFFICE

(12)          CERTIFICATE EXTENDING PATENT TERM
UNDER 35 U.S.C. § 156

| | | | |
|---|---|---|---|
| (68) | PATENT NO. | : | 5,214,052 |
| (45) | ISSUED | : | May 25, 1993 |
| (75) | INVENTOR | : | Kunihiko Ofuchi, et al. |
| (73) | PATENT OWNER | : | Mitsubishi Chemical Corporation |
| (95) | PRODUCT | : | Acova (argatroban) |

This is to certify that an application under 35 U.S.C. § 156 has been filed in the United States Patent and Trademark Office, requesting extension of the term of U.S. Patent No. 5,214,052 based upon the regulatory review of the product Acova (argatroban) by the Food and Drug Administration. Since it appears that the requirements of the law have been met, this certificate extends the term of the patent for the period of

(94)                      1,497 days from May 25, 2010, the original expiration date of the patent, subject to the payment of maintenance fees as provided by law, with all rights pertaining thereto as provided by 35 U.S.C. § 156(b).

I have caused the seal of the United States Patent and Trademark Office to be affixed this 12th day of October 2005.

Jon W. Dudas
Under Secretary of Commerce for Intellectual Property and Director of the United States Patent and Trademark Office

UNITED STATES PATENT AND TRADEMARK OFFICE

(12)          CERTIFICATE EXTENDING PATENT TERM
UNDER 35 U.S.C. § 156

| | | | |
|---|---|---|---|
| (68) | PATENT NO. | : | 5,214,052 |
| (45) | ISSUED | : | May 25, 1993 |
| (75) | INVENTOR | : | Kunihiko Ofuchi, et al. |
| (73) | PATENT OWNER | : | Mitsubishi Chemical Corporation |
| (95) | PRODUCT | : | Acova (argatroban) |

This is to certify that an application under 35 U.S.C. § 156 has been filed in the United States Patent and Trademark Office, requesting extension of the term of U.S. Patent No. 5,214,052 based upon the regulatory review of the product Acova (argatroban) by the Food and Drug Administration. Since it appears that the requirements of the law have been met, this certificate extends the term of the patent for the period of

(94)          1,497 days from May 25, 2010, the original expiration date of the patent, subject to the payment of maintenance fees as provided by law, with all rights pertaining thereto as provided by 35 U.S.C. § 156(b).

I have caused the seal of the United States Patent and Trademark Office to be affixed this <u>12th day</u> of <u>October 2005</u>.

Jon W. Dudas
Under Secretary of Commerce for Intellectual Property and Director of the United States Patent and Trademark Office